United States Patent [19]
Kondratyev

[11] Patent Number: 5,502,037
[45] Date of Patent: Mar. 26, 1996

[54] PRO-CYTOTOXIC DRUG CONJUGATES FOR ANTICANCER THERAPY

[75] Inventor: Alexi Kondratyev, Silver Spring, Md.

[73] Assignee: Neuromed Technologies, Inc., Silver Spring, Md.

[21] Appl. No.: 88,646

[22] Filed: Jul. 9, 1993

[51] Int. Cl.$^6$ .................. A61K 38/18; C07K 17/02; C07K 14/48
[52] U.S. Cl. ................. 514/21; 514/2; 514/8; 514/12; 530/345; 530/391.1; 530/391.9; 530/391.7; 530/399; 530/405; 530/409
[58] Field of Search .................. 514/21, 12, 8, 514/2; 530/345, 399, 395, 391.1, 391.9, 391.7, 408, 409, 410, 405; 424/85.91, 178.1

[56] References Cited

U.S. PATENT DOCUMENTS

| | | | |
|---|---|---|---|
| 4,545,985 | 10/1985 | Pastan et al. | 424/85 |
| 4,975,278 | 12/1990 | Senter et al. | 424/94.3 |
| 5,087,616 | 2/1992 | Meyers et al. | 514/21 |
| 5,120,740 | 6/1992 | Elfarra | 514/262 |

FOREIGN PATENT DOCUMENTS

| | | |
|---|---|---|
| 0441218 | 8/1991 | European Pat. Off. . |
| 88/07378 | 10/1988 | WIPO . |
| 90/05522 | 5/1990 | WIPO . |

OTHER PUBLICATIONS

Gould et al (1989) J. Natl. Cancer Inst. 81(10):775–781.
Osband et al (1990) Immunology Today 11(6):193–195.
Kaneko et al (1991) Bioconjugate Chem. 2(3):133–141.
Bagshawe et al (1988) Br. J. Cancer 58:700–703.
Senter et al., "Generation Of Cytotoxic Agents By Targeted Enzymes", *Bioconjugate Chem.*, vol. 4:3–9, (1993).
Svensson et al., "Monoclonal Antibody–β–Lactamase Conjugates For The Activation Of A Cephalosporin Mustard Prodrug", *Bioconjugate Chem.*, vol. 3:176–181, (1992).
Wallace et al., "In Vitro And In Vivo Activities Of Monoclonal Antibody–Alkaline Phosphatase Conjugates In Combination With Phenol Mustard Phosphate", *Bioconjugare Chem.*, vol. 2:349–352, (1991).
Senter, "Activation Of Prodrugs By Antibody–Enzyme Conjugates: A New Approach To Cancer Therapy", *The FASEB Journal*, vol. 4:188–193 (1990).
Brock, "Comparative Pharmacologic Study In Vitro An In Vivo With Cyclophosphamide (NSC–26271), Cyclophosphamide Metabolites, And Plain Nitrogen Mustard Compounds", *Cancer Treatment Reports*, vol. 60:301–308, (1976).
Alarcon et al., "Isophosphamide As A New Acrolein–Producing Antineoplastic Isomer Of Cyclophosphamide", *Cancer Research*, vol. 32:2519–2523, (1972).
Hill et al., "Metabolism Of Iphosphamide [2–(2–Chloroethylamino)–3–(2–Chloroethyl)tetrahydro–2H–1,3,2–oxazaphosphorine 2–Oxide] And Production Of A Toxic Iphosphamide Metabolite", *Cancer Research*, vol. 33:1016–1022, (1973).
Alarcon et al., "Effects Of Diazoxide And A Dipyridamole Derivative On Cardiac Nucleotide Content", *Nature New Biology*, vol. 233:250–252, (1971).
Yankner et al., "The Biology And Mechanism Of Action Of Nerve Growth Factor", *Ann. Rev. Biochem.*, vol. 51:845–868, (1982).
Rakowicz–Szulczynska, "Identification Of The Cell Surface And Nuclear Receptors For NGF In A Breast Carcinoma Cell Line", *Journal Of Cellular Physiology*, vol. 154:64–70, (1993).
Greene et al., "PC12 Pheochromocytoma Cells: Culture, Nerve Growth Factor Treatment, And Experimental Exploitation", *Methods In Enzymology*, vol. 147:207–216, (1987).
Marchetti et al., "Nerve Growth Factor Receptors In Human Neuroblastoma Cells", *Journal Of Neurochemistry*, vol. 49:475–486, (1987).
Waldmann, "Monoclonal Antibodies In Diagnosis And Therapy", *Science*, vol. 252:1657–1662, (1991).
Hird et al., "Immunotherapy With Monoclonal Antibodies", *Genes And Cancer*, pp. 002–008, (1990).
Wilman (1986) "Prodrugs in Cancer Chemotherapy", Biochem. Soc. Trans. 14: 375–382.

*Primary Examiner*—Kay K. A. Kim
*Attorney, Agent, or Firm*—Foley & Lardner

[57] ABSTRACT

Pro-cytotoxic drug conjugates for anticancer therapy comprising a homing agent first moiety, a spacer molecule second moiety covalently linked to the homing agent, and a third moiety covalently linked to the second moiety consisting of a pro-cytotoxic drug that is non-toxic extracellularly but that, after internalization of the conjugate by proliferating tumor cells, is metabolized by one or more endogenous intracellular enzymes to a cytotoxic metabolic product, so that cell growth is arrested or the cells killed. Preferred procytotoxic drugs are carboxyphosphamide or carboxyisophosphamide.

8 Claims, No Drawings

PRO-CYTOTOXIC DRUG CONJUGATES FOR ANTICANCER THERAPY

BACKGROUND OF THE INVENTION

1. Field of the Invention

The present invention relates to chemical conjugates for the selective delivery of anticancer drugs to tumor cells. More particularly, the invention relates to chemical conjugates for the delivery of non-toxic pro-cytotoxic drugs to target tumor cells that are metabolized by intracellular endogenous enzymes to cytotoxic drugs.

2. Description of the Background Art

It is well known in current chemotherapy protocols to administer anti-mitotic drugs such as adriamycin, vincristine, cisplatin, doxorubicin, daunomycin and methotrexate, toxins such as diphtheria toxin, pseudomonas toxin and ricin, and anti-tumor drugs such as cyclophosphamide and isophosphamide in cancer chemotherapy. Unfortunately, these drugs also have acute undesirable side effects on the normal cells of the patient, thus severely limiting the doses that can safely be administered. For a review, see DeVita, "Principles of Cancer Therapy", pages 765–788, in Petersdorf et al., *Principles of Internal Medicine*, 10th ed., McGraw-Hill, N.Y., 1983. In addition, many tumor cells are known to exhibit or to develop multidrug resistance, which also limits the effectiveness of cancer chemotherapy. For a review, see Kane et al, *J. Bioenerget. Biomembr.*, 22:593 (1990).

Many approaches have been explored to improve the effectiveness and specificity of cancer chemotherapy. One approach has been to attempt to specifically direct anticancer drugs to malignant cells, so that their effect on normal cells would be minimal; this approach is generally referred to as "drug targeting." In one example of this approach, the anticancer drug is conjugated to a homing agent which is an antibody, preferably a monoclonal antibody ("mAb"), that is selected to be complementary to a tumor-associated or tumor-specific antigen. It is expected that the cytotoxic drug will be released from the conjugate at the tumor cells, and thereafter exert its toxic effects on the target cells. There are, however, several disadvantages to using antibodies as delivery agents. Internalization of antibody conjugates into cells is unpredictable. Tumor-associated antigens may be heterogeneous. The antibody itself may be antigenic and produce an undesirable immune response in the patient. The antibody might bind via its Fc receptors even to normal cells lacking the target antigen. It is difficult to attach a large number of drug molecules to an antibody without compromising the latter's complementariness. Finally, the high molecular weight of antibodies results in slow diffusion through body spaces and into solid tumor masses.

In another example of the aforementioned targeting approach, the drug is conjugated to a biodegradable polyamino acid macromolecular carrier or to such a polyamino acid carrier that is also linked to a homing agent. Theoretically, degradation of the polyamino acid carrier in the target cells releases the cytotoxic drug. Unfortunately, the use of a polyamino acid carrier encounters many of the aforementioned problems associated with the use of antibodies as drug carriers. Such bulky polyamino acid carriers may reduce the ability of the conjugate to penetrate many tumors efficiently, particularly when the conjugate also contains a protein homing agent.

It is also known to directly conjugate toxins to non-immunoglobulin homing agents, generally peptides, proteins, growth factors or hormones that react with specific cell receptors. Unfortunately, such delivery systems also generally show high and unpredictably variable toxicity for normal cells, as well as for tumor cells, in part because of a multiplicity of target cells for many of the aforementioned agents and in part because of extracellular release of the toxin.

An alternate strategy is to use a mAb as a delivery agent for an enzyme that is theoretically capable of generating within tumor masses low molecular weight cytotoxic drugs from concurrently or sequentially administered relatively noncytotoxic precursors ("prodrugs" or "procytotoxic drugs"). The drugs generated in this manner would be theoretically expected to diffuse into tumor cells and cause their growth inhibition or death (for a review, see Senter et al., *Bioconjugate Chem.*, 4:3 (1993)). Unfortunately, plasma and other normal tissues are often capable of activating the prodrugs, due in part to the presence elsewhere of the converting enzyme and in part to the binding of antibody-enzyme conjugate at non-tumor sites, likely through Fc receptors (see, e.g., Antoniw et al., *Brit. J. Cancer*, 62:909 (1990)). In addition, the targeted enzymes are generally of microbial origin (U.S. Pat. No. 4,975,278), thus potentially producing antibody responses in humans.

It would be highly desirable to have available a drug delivery system that delivers a chemotherapeutic drug primarily to tumor cells, in which the drug is essentially innocuous extracellularly or even in normal cells, and in which the drug is innocuous even in tumor cells until one or more endogenous intracellular enzymes concentrated in tumor cells converts the prodrug into a cytotoxic drug. Such a drug delivery system has been discovered and is described below.

SUMMARY OF THE INVENTION

The invention resides in destroying or reducing the growth rate of highly proliferating tumor cells, but not normal cells, with a composition that includes a novel multicomponent pro-cytotoxic drug conjugate comprising:

a) a first moiety which is a protein or peptide homing agent that preferentially binds to tumor cells;

b) a second moiety which is a spacer molecule covalently bound to the first moiety at a site that does not participate in the binding of the homing agent to its tumor cell binding sites; and c) a third moiety which is a pro-cytotoxic drug molecule covalently bound to the spacer molecule, wherein the conjugate is internalized primarily by target tumor cells bearing binding sites for the homing agent, and wherein the pro-cytotoxic drug member of the conjugate is not toxic or only marginally toxic extracellularly or in normal cells, but is metabolized primarily in proliferating tumor cells by one or more endogenous enzymes to a cytotoxic form, so that the growth of the tumor is arrested or the cells are killed.

In one aspect of the conjugates of the invention, first moiety homing agents are described, the homing agents preferentially being proteins or polypeptides that bind specifically to target tumor cell receptors or other tumor tissue specific binding sites.

In another aspect of the conjugates of the invention, second moiety spacer molecules are described, these molecules preferentially being homobifunctional or heterobifunctional molecules capable of covalent binding to both the homing agent and the pro-cytotoxic drug in such manner as not to interfere with the functioning of either moiety.

In another aspect of the conjugates of the invention, there is described third moiety procytotoxic drugs that are nontoxic to normal or tumor cells in the pro-form but that are converted, after internalization of the conjugate by tumor cells, to cytotoxic forms by endogenous enzyme(s).

It is yet another aspect of the invention to use the aforementioned conjugates in methods of treating tumor cells.

These and other aspects of the invention will become apparent by reference to the detailed description of the invention and the appended claims.

DETAILED DESCRIPTION OF THE INVENTION

Applicant has discovered that the difficulties attendant upon the use of previously known anticancer chemotherapeutic compounds and conjugates can be largely overcome by the use of the novel chemotherapeutic drug conjugates of the invention. These conjugates are based on three moieties that are linked covalently in particular manners.

The first moiety is a homing agent that will specifically target the prodrug-containing conjugate to tumor cells containing large numbers of specific receptors or binding sites for the homing agent, or high concentrations of tumor-specific binding sites. The binding target molecule to which the prodrug-containing conjugate is directed should ideally be a widely expressed component of the cancer cell and one that is not secreted into body fluids. It is highly preferred in this invention that the drug conjugate be efficiently internalized by the target cell, such as by receptor-mediated endocytosis. It is preferred, therefore, that the homing agent, once in contact with its cellular binding site, promote internalization of the conjugate.

The internalizable homing agent may be a peptide or protein growth factor, cytokine, tumor-specific antigen, hormone, transfer protein or antibody. It should be noted that the tumor cells to which these homing agents will bind differ from agent to agent, a fact that should be considered when selecting a particular homing agent to incorporate into a conjugate of the invention. Homing agents suitable for the conjugates of the invention include nerve growth factor (NGF), for which large numbers of internalizable receptors are present on the surface of neuroblastoma, undifferentiated glioma, pheochromocytoma, melanoma tumor and breast carcinoma cells (see, e.g., Vinores et al., *Cancer Lett.*, 10:309 (1980); Vinores et al., *J. Cancer Res. Clin. Oncol.*, 98:54 (1980); Koestner et al., *Toxicol. Pathol.*, 13:90 (1985); Kondratyev, *Trans. Amer. Soc. Neurochem.*, 23:236 (1992); and Rakowicz-Szulzynska, *J. Cell. Physiol.*, 154:64 (1993)). Other preferred homing agents include epidermal growth factor (EGF), α-transforming growth factor (α-TGF), or vaccinia virus growth factor (VVGF), all of which exhibit high affinity binding to, and rapid internalization into, tumor cells bearing EGF receptors, such as rapidly proliferating squamous cell carcinomas, lung cancers, and sarcomas (U.S. Pat. No. 5,087,616). Another preferred homing agent is platelet-derived growth factor (PDGF), which binds to, and is internalized by, a variety of neoplastically transformed cells such a glioma, osteosarcoma, embryonal carcinoma and transformed fibroblasts (see, e.g, Nilsson et al., *PNAS (USA)*, 80:5592 (1983); Van Zoelen et al., *Med. Cell Biol.*, 5:2297 (1985)). It is intended that the conjugates of this invention will include as homing agent any protein or polypeptide growth factor that is a ligand for (i.e., binds to) receptors or other binding sites concentrated on tumor cell plasma membranes or contained within such cells.

The homing agent of the invention may also be a tumor-specific antigen such as α-fetoprotein that will target tumor cells such as human β-lymphoma and T-cell leukemia cells, a prostate specific antigen that will concentrate in prostate adenocarcinoma cells, a carcinoembryonic antigen (CEA), or a transfer carrier protein such as transferrin which binds to tumor cells such as T-cell leukemia cells and is internalized. See, e.g., Torres et al., *Int. J. Cancer*, 50:418 (1989); Estaban et al., *J. Biol. Chem.*, 267:10177 (1992); Gueskens et al., *Eur. J. Cell Biol.*, 50:418 (1989).

Hormones may also serve as homing agents in the invention. For example, alpha melanocyte-stimulating hormone (α-MSH) targets melanoma cells and is internalized by these cells. Murphy et al., *Proc. Natl. Acad. Sci. (USA)*, 83:8258 (1986). Suitable in practicing this invention is any peptide hormone that will target tumor tissue, such as insulin or insulin-like growth factor; glucagon; thyrotropin (TSH) or thyrotropin releasing hormone (TRP); somatostatin; calcitonin; lysine bradykinin, and the like. All of the preferred homing agents mentioned above are commercially available through Sigma Chemical Co., St. Louis, Mo., Calbiochem Co., La Jolla, Calif., and ICN Biomedical Co., Irvine, Calif., or can be isolated or synthesized by methods well known in the art, including recombinant DNA methods.

In summary, the following general criteria should be considered in selecting a homing agent for this invention:

a) it should be directed preferentially to tumor cells and not to normal cells;

b) it should bind to specific binding sites present in a wide range of tumor cell types;

c) it should promote the internalization of the drug conjugate of which it is a member;

d) it should be of size sufficiently small so as not to impede passage of the conjugate into solid tumors; and, e) suitable chemistry must exist for coupling the homing agent to the other components of the conjugate in a manner so as not to interfere with the binding of the homing agent to its target binding site or the metabolism of the pro-drug to its toxic form.

The second moiety in the drug conjugate of the invention consists of one or more spacer molecules that serve to link the homing agent to a plurality of units of the third moiety, a pro-cytotoxic drug. The spacer compound should contain functional groups that can be covalently attached both to an appropriate site on the homing agent and to an appropriate chemical group on the pro-cytotoxic drug. The points of attachment to the homing agent and to the pro-cytotoxic group should be those that are not involved in the binding to target cells or enzymatic conversion of the pro-drug to the cytotoxic drug, respectively.

The nature of the linkage between homing agent and spacer molecule and between spacer molecule and prodrug depends on the functionality employed in the homing agent and prodrug. Primary amine functionalities of homing agent and prodrug are normally employed in secondary amide linkage with a terminal carboxyl group of a homobifunctional spacer molecule. Similarly, carboxyl functionalities of homing agent or prodrug are normally employed in secondary amide linkage with a terminal amine group of a homobifunctional spacer molecule, as in formulae I and II below. Spacer molecules may also be heterobifunctional and link to homing agent and to prodrug via different functional groups.

A preferred spacer moiety in the invention where the functional groups to be linked are both carboxyl groups is a homobifunctional primary diamine of the formula (I) below:

$$H_2N-(CH_2)_n-NH_2 \qquad (I)$$

wherein n is in the range of 2 to 20; preferably n is 4 to 8. When present in the conjugate, the second moiety may appear as in formula II below:

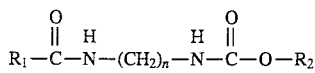  (II)

wherein n is as above,

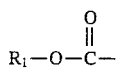

is derived from a free carboxyl of the first moiety (e.g., C-terminal carboxyl group of a protein or polypeptide homing agent), wherein $R_1$ is a homing agent and

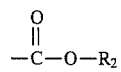

is derived from a free carboxyl group of a pro-cytotoxic drug wherein $R_2$ is a pro-cytotoxic drug, Alternately, the spacer moiety may be a heterobifunctional compound, such as in formula III below:

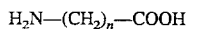  (III)

wherein n is as described in formula (I) above. With this carrier compound, in one embodiment the primary amino group is linked in secondary amide linkage to a carboxyl group of the homing agent or prodrug moiety and the carboxyl group is linked in secondary amide linkage to an amino group of the prodrug or homing agent moiety, respectively. Prodrugs bearing a hydroxyl function are linked similarly to spacer molecules as esters, or through carbonate linkages. Those skilled in this art will undoubtedly be familiar with other suitable spacer compounds.

It is important that the spacer moieties used in the invention contain internal groups that are not labile under physiological conditions, that is, they should not be subject to scission extracellularly or on cell surfaces by enzymes. For example, spacer molecules should not contain disulfide groups that may be reduced or be subject to thiol interchange reactions; however, if such a disulfide spacer is desired, phenyl or methyl groups, or both, should be disposed adjacently to a disulfide bond so as to restrict access by enzymes to this bond. A good description of the use of such bridging agents can be found in the Pierce Chemical Co. (Rockford, Ill.) *Handbook and General Catalog* (1989), pp. 283–312.

A preferred coupling reagent for producing the aforementioned amide linkage is the well-known water-soluble 1-ethyl-3-(3-dimethylaminopropyl) carbodiimide (EDC, Pierce Chem. Co.). Suitable spacer molecules are commercially available from Pierce Chemical Co., Aldrich Chemical Co., Milwaukee, Wis., and Merck & Co., Rahway, N.J.

Appropriate monoclonal antibodies (mAbs) may also serve as homing agents for the prodrug conjugates of the invention. As used herein, an "appropriate" antibody is one which: (i) is specifically directed to a tumor cell antigen; (ii) is essentially non-immunogenic in the recipient subject; (iii) is unaffected as to complementariness by linkage to a spacer moiety; (iv) binds minimally to non-tumor tissues; (v) is internalized by the target tumor cells; and (vi) remains intact during the passage from the site of parenteral administration to target cells. It is preferred that the aforementioned antibody be a mAb directed to an epitope on a tumor-specific surface antigen. Methods for identifying and isolating tumor-specific antigens are well known in the art. For reviews, see Waldmann, *Science,* 252:1657 (1991); Hird et al., *Genes and Cancer,* Wiley, N.Y. 1990; Sedlacek, *Contributions to Oncology,* vol. 25, Karger, N.Y., 1987; Willingham et al., *J. Histochem. Cytochem.,* 37:928 (1989).

To avoid or reduce undesired antibody responses in recipients of antibody-containing conjugates with prodrugs, in one preferred embodiment the aforementioned mAb may be "humanized," that is to say, the mAb is produced in a form that is essentially non-immunogenic in human subjects. This may be accomplished by art-recognized methods. In one approach, spleen cells from tumor specific antigen-immunized animals may be immortalized by fusion with human myeloma cells. In another approach, human antibodies may be produced in SCID-hu mice (see, e.g., McCane et al., *Science,* 241:1632 (1988); Mosier et al., *Nature,* 35:256 (1988)). Alternately, light and heavy chains from the variable regions of a humanized mAb may be reproduced by recombinant DNA methods (for reviews, see, e.g. Winter et al., *Nature,* 349:293 (1991); Mallinax et al., *PNAS (USA),* 87:8095 (1990); Waldmann (1991) above. Fragments of mAbs may be derived by well-known methods of genetic engineering by using cloned cDNA sequences encoding the V regions of the antibody. A fragment corresponding to $V_H$ alone may be used as a single chain antibody lacking the Fc portion, thus greatly reducing non-specific binding and increasing tumor tissue penetration (see, e.g., Chiang, *Bio/Techniques,* 7:360 (1989)).

Where antibodies or fragments thereof serve as homing agents, it is advantageous that these materials, just as previously-described homing agents, be linked to prodrugs via stable spacer molecules that interfere with neither antibody-target cell binding nor the metabolic conversion of the prodrug to the cytotoxic drug. The ability of these immuno conjugates to be internalized by target tumor cells may be tested in vitro with human tumor cell lines by methods well-known in this art. In vivo tests using tumor-bearing laboratory animals may be accomplished by art-recognized methods, including testing for tumor size regression following parenteral administration of the immuno conjugate.

By "pro-cytotoxic drug" or "pro-drug" is meant herein a drug that is relatively innocuous to cells while still in the parent form but which is metabolized by one or more endogenous intracellular enzymes located within target tumor cells to a metabolic product that is cytotoxic to such a cell. By "endogenous enzyme" is meant an enzyme normally occurring within a cell. It is not intended to include an exogenously administered enzyme that enters cells. The target tumor cells will contain the endogenous enzyme(s) required for this conversion and the catalytic activity of this enzyme(s) should be sufficiently high so as to produce cytotoxic concentrations of the drug. Testing of cell extracts for enzyme activity may be accomplished by conventional methods. The term pro-cytotoxic drug or pro-drug as used herein is not intended to include drugs that are not metabolized to a cytotoxic form, but are merely released intact from a carrier by, e.g., a hydrolytic enzyme. By "cytotoxic" is meant herein arresting the growth of, or killing, cells.

Although it is intended that the conjugates of the invention include any pro-cytotoxic drug (as defined above), highly preferred are carboxyphosphamide ("CPA") and its homologs and derivatives, such as are described in Table I below.

TABLE I

Structure of Carboxyphosphamide and Its Homologs and Derivatives

Cl—CH$_2$—CH$_2$\  
          N—P=O  
      R /   \ NH  
                |  
                R$^1$

O—CH$_2$\  
      CH—R$^2$  
    /  
COOH

| Compound | R | R$^1$ | R$^2$ |
|---|---|---|---|
| I | CH$_2$CH$_2$Cl | H | H |
| II | CH$_2$CH$_2$Cl | CH$_2$CH$_2$Cl | H |
| III | CH$_2$CH$_2$Cl | H | CH$_3$, CH$_2$CH$_3$ |
| IV | CH$_2$CH$_2$Cl | H | Phenylketo |
| V | H | CH$_2$CH$_2$Cl | H |
| VI | H | CH$_2$CH$_2$Cl | Phenylketo |

The parent of carboxyphosphamide, namely, cyclophosphamide itself (1 in Scheme IV) exhibits only slight biologic activity in vitro and in vivo initially, but becomes highly cancerotoxic as the result of its in vivo metabolism, primarily in the liver, to cytotoxic products (Scheme IV) (Brock, *Laval Med.*, 139:696 (1968); Brock, *Cancer Treat. Rep.*, 60:301 (1976)). The cytotoxic products have been identified as acrolein 7 and nor-nitrogen mustard 8 in Scheme IV (Brock, 1976; Alcarcon et al., *Nature New Biology*, 233:250 (1971)).

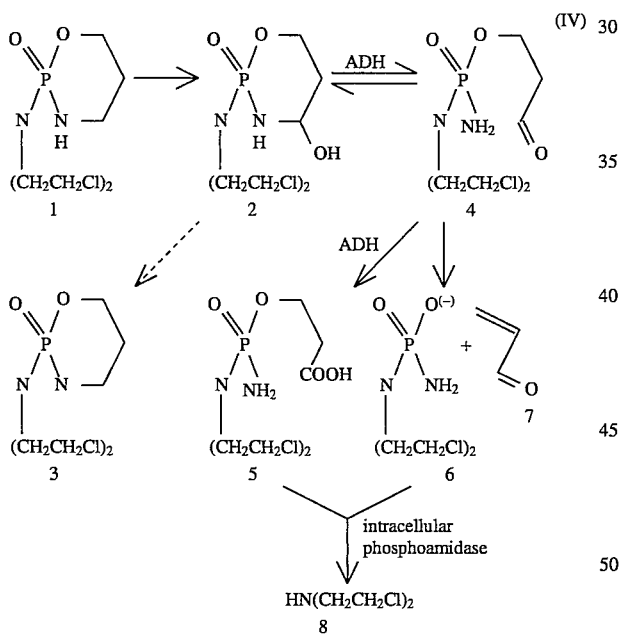

Referring to scheme IV above, cyclophosphamide 1 is oxidized in liver microsomes, in a process involving cytochrome P-450, to 4-hydroxy cyclophosphamide 2. Although 2 can be partially transformed into the low cytotoxic 4-heterocyclophosphane 3, most of 2 is reversibly converted into the "aldo" form 4 by the enzyme alcohol dehydrogenase. The "aldo" form 4 formed extracellularly can be spontaneously cleaved to form the toxic acrolein 7 and phosphoramidomustard 6, both of which can freely enter normal, as well as tumor, cells. Within cells, phosphoramidomustard 6 is cleaved by the enzyme phosphoamidase to produce highly cytotoxic nor-nitrogen mustard (NNM, 8). The cytotoxicity of NNM is based upon its ability to covalently crosslink two guanine residues of mRNA, thus preventing translation of DNA. This is the basis for the general cytotoxicity of cyclophosphamide.

The "aldo" form 4 is also convertible to carboxyphosphamide 5 ("CPA"). However, circulating CPA is not toxic per se, does not enter cells in significant amounts, is not metabolized extracellularly, and is normally entirely excreted from the body via the kidneys. This accounts for the low toxicity of CPA. It has been found unexpectedly that, when CPA is brought into tumor cells by the conjugate of the invention, it can be acted on directly by an endogenous intracellular phosphoamidase to produce highly cytotoxic NNM 8, thereby accounting for the effect of intracellular CPA in arresting tumor cell growth or killing such cells.

We have found unexpectedly that CPA is degraded to cytotoxic NNM primarily in cells that contain large amounts of phosphoamidase activity. Actively proliferating cells, such as tumor cells, but not normal cells such as nerve cells, contain highly active phosphoamidase enzyme (Gomori, G., *Proc. Soc. Exp. Biol. Med.*, 69: 407–9 (1948). We have discovered that CPA is potentially cytotoxic (i.e., a pro-cytotoxic drug) primarily in proliferating tumor cells. CPA is commercially available from Asta-Medica AG, Frankfurt, Germany.

A comparison of the published toxicities of various cyclophosphamide metabolites is shown in Table II.

TABLE II

Biological Activities of Cyclophosphamide and Its Metabolites

| | In vitro activities | | In vivo activities | | D50 |
|---|---|---|---|---|---|
| Drug | Alkylating (%) | Cytotoxicity (CU/μmol) | CD50 (mg/kg) | LD50 (mg/kg) | Index (LD50/CD50) |
| CP | 1.3 | <0.03 | 1.25 | 220 | 175 |
| 4-OH CP | 65 | 63 | 1.25 | 150 | 120 |
| CPA | 85 | 0.1 | 200 | ~800 | ~4 |
| Acrolein | (1.9) | 0.4 | >2.15 | 7.3 | ~3 |
| NNM | 100 | 1.35 | 40 | 100 | 2.5 |

Taken from Brock, 1976.  
Alkylation: by the NBP test (relative to NNM).  
In vitro cytotoxicity: cu = cytostatic units, against mouse Yoshida ascites sarcoma cells.  
In vivo: CD$^{50}$ = curative dose; LD$^{50}$ = lethal dose; D$^{50}$ = therapeutic index; Yoshida ascites sarcoma in rat.

The data of Table II indicate that CPA is virtually inactive in both the in vitro Yoshida cell cytotoxicity test and in vivo against the rat Yoshida ascites sarcoma, likely because, as noted above, CPA per se enters cells only poorly. CPA is, however, a strong alkylating agent when used in the NBP test. However, as will be detailed below in Example 2, once CPA is internalized in the form of the inventive conjugate, it becomes a powerful cytotoxic agent against tumor cells. The data also demonstrate, as described above, that the parent drug, CP, is virtually inactive in the cytotoxicity test, but, when activated in vivo, is a highly active therapeutic agent.

A homolog of cyclophosphamide, namely, isophosphamide (cpd. V of Table I; cpd. 9 of Scheme (V)) is highly cytotoxic in vivo to tumor cells once activated (Brock, 1968; Alarcon et al., *Cancer Res.*, 2514 (1972); Hill et al., *Cancer Res.*, 33:1016 (1976)). Metabolism of isophosphamide in tissue produces cytotoxic intermediates analogous to those produced in cyclophosphamide metabolism. In tissues, isophosphamide 9 is first oxidized to the 4-hydroxy and 4-keto intermediates; oxidation of the 4-keto compound produces aldo-isophosphamide 10. Further oxidation of 10 produces both acrolein and carboxy isophosphamide 11 (CIPA). Enzyme-catalyzed cleavage of 11 yields the cytotoxic phosphonitrogen mustard homolog 12. the conjugate of the invention may, therefore, use CIPA as the pro-cytotoxic drug. CIPA and other homologs and derivatives of carboxyphosphamide are available commercially from Asta-Medica A.G.

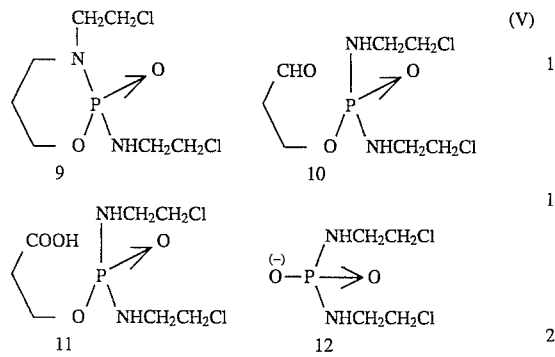

Phenylketo and 3-alkyl derivatives of CPA and CIPA are effective pro-drugs in the conjugative of the invention.

We have found that the polypeptide nerve growth factor (NGF) is highly effective in targeting a CPA conjugate to human melanoma cells, neuroblastoma cells, pheochromocytoma cells, undifferentiated glioma cells and breast carcinoma cells. It is known that human melanoma cells carry large numbers (up to about $1 \times 10^6$) of NGF receptors (see, e.g., Grob et al., *J. Biol. Chem.*, 258:14136 (1983), and that neuroblastoma, melanoma, colon carcinoma cells, breast carcinoma cells and pheochromocytoma cells have high affinity internalizable NGF receptors (see, e.g., Marchetti et al., *J. Neurochrom.*, 49:475 (1987); Yankner et al., *Ann. Rev. Biochem.*, 51:845 (1982); Rakowicz-Szulczynska et al., *PNAS (USA)*, 83:3728 (1986)). Nerve cells and other normal cells normally do not proliferate (and have low levels of phosphoamidase activity), and other human cells types either do not carry NGF receptors (normal melanocytes), or have only low affinity binding that does not lead to internalization (such as spleen mononuclear cells, macrophages, Schwann cells, peritoneal mast cells) (see, e.g., Bruni et al., *FEBS Lett.*, 138:190 (1982); Thorpe et al., *J. Neurosci. Res.*, 17:128 (1987); Yasuda et al., *Brain Res.*, 435:113 (1987)). Therefore, it is highly preferred in this invention to use NGF as a homing agent for the delivery of the pro-cytotoxic conjugates of the invention to the aforementioned tumor cells.

Chemical modification of the carboxyl groups of NGF does not interfere with its receptor binding ability, while amino group modification leads to complete loss of binding activity for receptors (see, e.g., Rosenberg et al., *J. Neurochem.*, 46:641 (1986)). Therefore, where the drug conjugate of the invention uses NGF as the first moiety, covalent binding between NGF and the spacer arm should utilize the carboxyl group of the NGF for linkage, but not its amino groups.

As will be detailed in the examples below, care must be taken to control the extent of derivatization i.e., molar ratios, in the Homing Agent-Spacer-Pro-Cytotoxic Drug conjugates of the invention. A series of conjugates of differing molar ratios can be produced, given the guidance contained herein, and screened in an in vitro model of a cell growth test system, such as by the incorporation of [$^3$H]-thymidine into cellular DNA of a tumor cell line. For NGF-containing conjugates a particularly suitable tumor cell line for this purpose is the PC12 pheochromocytoma cell line (see Example 2 below), which is known to be reflective of in vivo tumor metabolism. Other similar human tumor cell lines will be well known to those skilled in this field.

The pro-cytotoxic drug conjugates of the invention may be formulated into pharmaceutical preparations with standard pharmaceutically acceptable buffers and excipients such as are described in *Remington's Pharmaceutical Sciences*, 18th ed., Mack Publ. Co., Easton, Pa., 1990, which is incorporated herein by reference. Conjugate formulations may be administered parenterally in dosages and in regimens appropriate to the clinical condition of the recipient. Such dosage regimens include, but are not limited to, about 0.1–10 mg of pro-cytotoxic drug per kg body weight.

The following examples are merely exemplary of several embodiments of the invention and are in no way intended to limit the scope of the invention, which is defined by the specification and appended claims.

EXAMPLE 1

Synthesis of NGF-HMDA-CPA Conjugates

The chemical reactions employed are shown in scheme (VI) below:

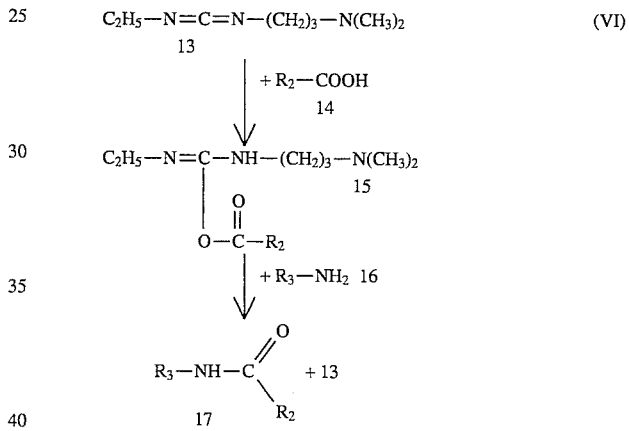

In Scheme (VI) above, in the first stage of the process, the carbodiimide coupling agent 13 (EDC) is first coupled to the carboxyl group of $R_2$ pro-drug 14, e.g., carboxyphosphamide (CPA), to form an intermediate coupling agent-pro-drug conjugate, 15. In the next step, intermediate 15 is coupled to the amino group of $R_3$ hexamethylenediamine (HMDA) 16, to form a conjugate 17 between pro-drug and HMDA; EDC is a by-product. In the second stage of the process, NGF is coupled, using EDC, to free amino groups of the HMDA moiety of the pro-drug-HMDA conjugate to form the final NGF-HMDA-pro-drug conjugate.

In one embodiment, EDC, HMDA and CPA were dissolved in 10 mM pyridine●HCl buffer (Buffer A): pH 5.0, at 4° C. to give final concentrations of 104 mM, 138 μM and 68 μM, respectively. For the 10:10:1 conjugate, 10 μl of HMDA solution was mixed with 124 μl of Buffer A. For a 10:50:1 conjugate, 50 μl of HMDA and 84 μl of Buffer A were mixed. For a 20:20:1 conjugate, 20 μl of HMDA and 94 μl of Buffer A were mixed. For a 20:40:1 conjugate, 40 μl of HMDA and 74 μl of Buffer A were mixed. EDC solution (13 μl) was added to the HMDA solution, mixed, and 20 μl (for the first two conjugates) or 40 μl (for the second two conjugates) of CPA solution were added. The reaction mixture was left overnight at 4° C. or 3 hours at room temperature, with stirring. Freshly made EDC solution (13 μl, 4 mg/ml) was added to the same tubes immediately followed by NGF (20 μl, 0.2 mg/ml) in deionized water. The mixture was stirred overnight at 4° C. The product was dialyzed three times against phosphate buffered saline for 24 hours, aliquoted, and stored at −70° C.

EXAMPLE 2

Effect of Pro-Cytocidal Drug Conjugates on the Growth of Pheochromocytoma Cells

PC12 pheochromocytoma cells were grown in DMEM supplemented with 7.5% of heat-inactivated horse serum (Gibco), 7.5% of fetal calf serum (Gibco), 50 μg/ml streptomycin (Serva), and 500 U/ml penicillin (Serva) in 75 cm² tissue culture flasks (Grainer) in an atmosphere of water-saturated 95% air—5% $CO_2$. 3T3 fibroblasts were grown according to Itkes et al., *Exp. Cell Res.*, 157:135 (1975).

The effect of conjugates on cell viability were determined either by Trypan blue exclusion (for the long term, i.e., >24 hours, effect) or by $^3$H-thymidine incorporation (for the short term, i.e., 3 hours, effect).

Conjugates of CPA:HMDA:NGF (Example 1) of various molar ratios were incubated in vitro with cells and the incorporation of [$^3$H]-thymidine into cell DNA measured at intervals. Data are presented as the percent effect relative to control, i.e. non-treated, cells. For $^3$H-thymidine incorporation, cells were plated on 96 well culture plates. $^3$H-thymidine (119 μCi/mmol) was added about 24 hours after seeding, and 10 minutes after beginning of the treatment of cells with conjugates for 3 hours; final concentration of the labeled precursor was 0.5 μCi/mL. After incubation, cells were washed twice with balanced Hank's solution, and transferred onto filters with a cell harvester (Titertek) for counting in an LKB LSS. Protein concentrations were determined according to Bradford, *Anal. Biochem.*, 72:248 (1976) for cell cultures, and according to Peterson, *Anal. Biochem.*, 70:346 (1977) for conjugates. The results are shown in Table 2.

TABLE 2

|   | CPA:HMDA:NGF (ratio) | Relative [$^3$H]-thymidine Incorporation (% of control at 3 hrs.) |
|---|---|---|
| 1. | 5:10:1 | 73.7 ± 2.1 |
| 2. | 10:10:1 | 48.0 ± 1.4 |
| 3. | 20:20:1 | 61.9 ± 2.8 |
| 4. | 5:10:1 | 112.1 ± 4.3 |
| 5. | 10:20:1 | 93.0 ± 3.2 |
| 6. | 20:40:1 | 59.4 ± 3.2 |
| 7. | 5:25:1 | 99.7 ± 4.1 |
| 8. | 10:50:1 | 45.5 ± 2.0 |
| 9. | 20:100:1 | 80.3 ± 2.1 |

The data show that all conjugates, with the exception of 4, 5 and 7, reduced cell growth when measured at the three hour incubation point; conjugates 2, 3, 6 and 8 were most effective. At 24 hours, all cells treated with conjugates 2 and 8 were dead (data not shown).

In parallel experiments, CPA (1 μM, 25 μM, 50 nM), HMDA (200 nM and 1 μM) and NGF (3.8 nM) alone, exhibited negligible cytotoxicity effects. The effects of conjugates and individual compounds on NGF receptor-negative 3T3 fibroblasts were also negligible, thus demonstrating that internalization of the conjugate is a prerequisite for cytotoxicity.

I claim:

1. A drug conjugate composition comprising:
   a) a first moiety polypeptide or protein tumor cell homing agent consisting of NGF;
   b) a second moiety spacer molecule covalently linked to said homing agent; and,
   c) a third moiety pro-cytotoxic drug covalently linked to said spacer molecule, wherein said pro-cytotoxic drug is a cyclophosphamide or cycloisophosphamide capable of being metabolized intracellularly by at least one endogenous enzyme normally present within said tumor cells to a cytotoxic metabolic product, wherein said conjugate binds to and is internalized by said tumor cell.

2. A composition of claim 1, wherein said second moiety spacer molecule is a homobifunctional or heterobifunctional organic molecule.

3. A composition of claim 2, wherein said homobifunctional molecule is an alkylene diamine.

4. A composition of claim 3, wherein said alkyklenediamine is hexamethylenediamine.

5. A composition of claim 1, wherein said pro-cytotoxic drug is carboxyphosphamide, carboxyisophosphamide, 3-phenylketocarboxyphosphamide, 3-phenylketocarboxyisophosphamide, 3-alkylcarboxyphosphamide or 3-alkylcarboxyisophosphamide.

6. A drug conjugate composition of the general structure:

wherein $R_1$—CO— is derived from a first moiety homing agent comprising NGF —NH—A—NH— represents a second moiety homobifunctional spacer molecule wherein A is hexamethylene, and wherein —CO—$R_2$ is derived from a third moiety carboxyphosphamide or carboxyisophosphamide.

7. A composition of claim 6, wherein the molar ratios of said first and second moieties to said third moiety range from 5–20:1 and 10–100:1, respectively.

8. A pharmaceutical composition, comprising the composition of claim 1 in a pharmaceutically acceptable vehicle.

* * * * *